(12) United States Patent
Chen (10) Patent No.: US 7,179,243 B2
(45) Date of Patent: Feb. 20, 2007

(54) SYRINGE WITH A SNAPPING DEVICE FOR BACKWARD PULLING THE NEEDLE INTO THE SYRINGE AFTER SYRINGING

(76) Inventor: Cho Ying Chen, P.O. Box 2103, Taichung (TW)

( * ) Notice: Subject to any disclaimer, the term of this patent is extended or adjusted under 35 U.S.C. 154(b) by 233 days.

(21) Appl. No.: 10/447,573

(22) Filed: May 9, 2003

(65) Prior Publication Data

US 2004/0225263 A1    Nov. 11, 2004

(51) Int. Cl.
*A61M 5/00*    (2006.01)
(52) U.S. Cl. ..................................... 604/110
(58) Field of Classification Search ............... 604/110, 604/187, 192, 195, 198
See application file for complete search history.

(56) References Cited

U.S. PATENT DOCUMENTS 5,395,337 A * 3/1995 Clemens et al. ............ 604/110
6,599,270 B1 * 7/2003 Chen ........................ 604/110

* cited by examiner

Primary Examiner—Kevin C. Sirmons
Assistant Examiner—Laura C. Schell
(74) Attorney, Agent, or Firm—Rosenberg, Klein & Lee (57) ABSTRACT

A syringe with a snapping device for backward pulling the needle into the syringe after syringing includes a hollow barrel having an annular shoulder laterally extending from an inner periphery near a front end and two sector apertures defined in and extending through the annular shoulder. The snapping device is detachably secured in the front end of the hollow barrel and includes an annular flange laterally extending therefrom. Two snappers downward extend from the snapping device and are engaged to the annular shoulder to longitudinally position the snapping device. A first connector is formed on the snapping device opposite the hollow stub. A plunger is slidably and partially received in the hollow barrel. A second connector extends from a bulb and is selectively connected to the first connector for turning and backward pulling the snapping device into the hollow barrel.

6 Claims, 13 Drawing Sheets

SYRINGE WITH A SNAPPING DEVICE FOR BACKWARD PULLING THE NEEDLE INTO THE SYRINGE AFTER SYRINGING

BACKGROUND OF THE INVENTION

1. Field of the Invention

The present invention relates to a syringe, and more particularly to a syringe with a snapping device for backward pulling the needle into the syringe after syringing.

2. Description of Related Art

Figure 19:
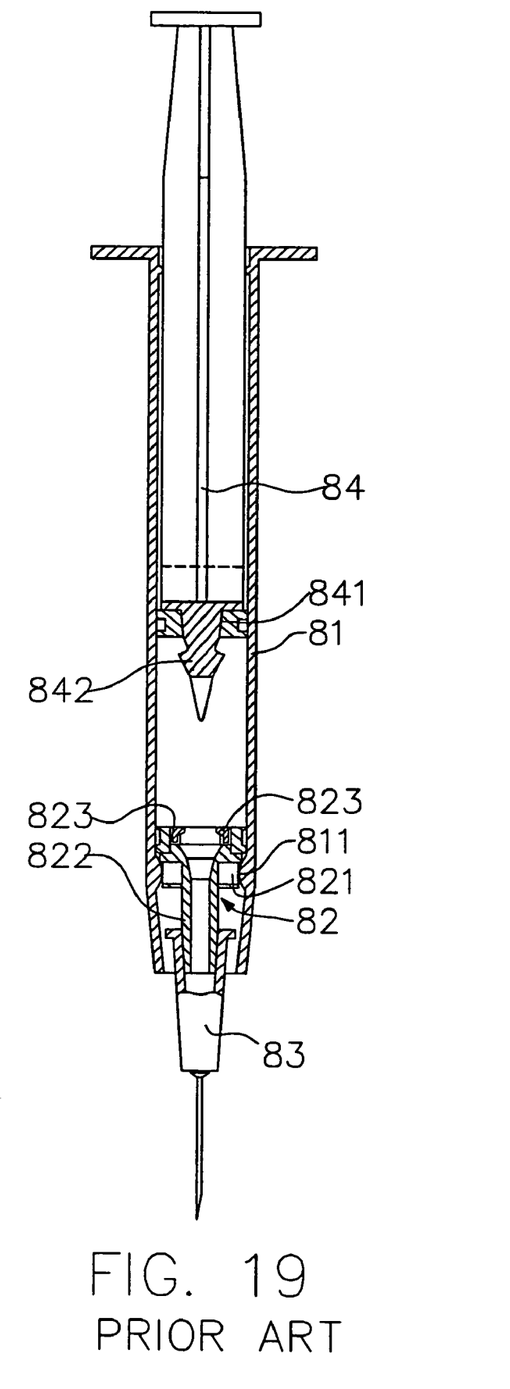
FIG. 19 is a side cross-sectional view of a syringe with a snapping device for backward pulling the needle into the syringe after syringing in accordance with the prior art.
Figure 20:
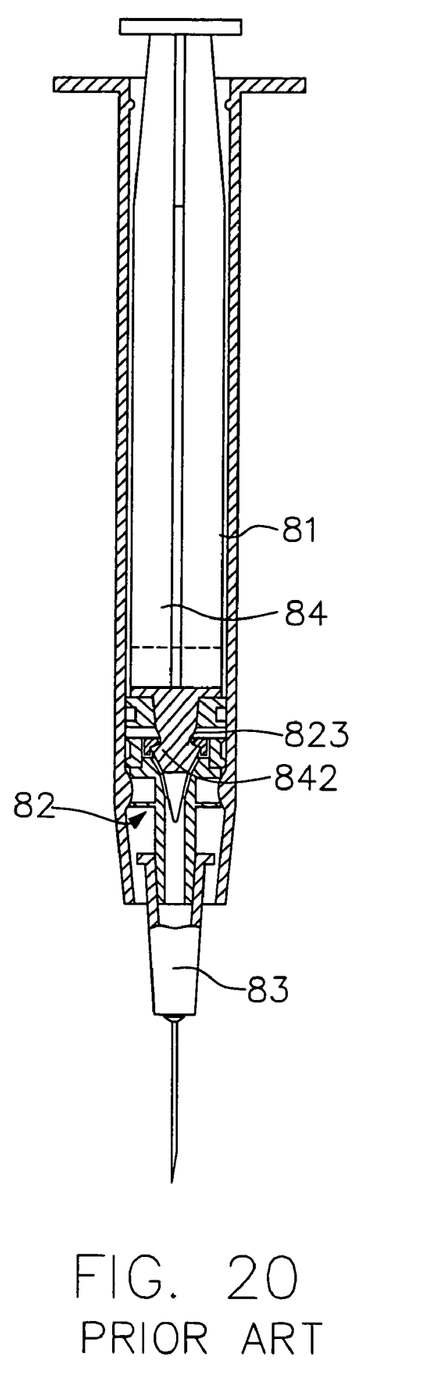
FIG. 20 is an operational cross-sectional view of the syringe in FIG. 19 when the plunger is connected to the snapping device of the syringe in FIG. 19.

A conventional syringe in accordance with the prior art shown in FIGS. 19 and 20 comprises a hollow barrel (81), a snapping device (82) secured in a first end of the hollow barrel (81), a needle hub (83) securely connected to the snapping device (82) and extending through the hollow barrel (81) and the plunger (84) movably received in the hollow barrel (81).

The hollow barrel (81) includes an annular protrusion (811) extending from the inner periphery of the hollow barrel (81). The snapping device (82) includes a body (not numbered) having a through hole (not numbered) centrically defined in the body. A concave (821) is defined in the outer periphery of the body to partially receive the protrusion (811) of the hollow barrel (81). A hollow stub (822) centrically extends from the body toward the first end of the hollow barrel (81). The needle hub (83) is securely connected to the hollow stub (822). The snapping device (82) includes an annular hook (823) from on an inner periphery of the through hole in the body of the snapping device opposite to the needle hub (83).

The plunger (84) includes a first end movably received in the hollow barrel (81) and a bulb (841) attached to the first end of the plunger (84). The bulb (841) abuts the inner periphery of the hollow barrel (81). An arrow (842) centrically extends from the bulb (841) toward the snapping device (82).

When finishing syringing, the arrow (842) is inserted into the through hole in the body of the snapping device (82) and engaged to the hook (823) to form a connection stronger than that between the annular protrusion (811) and the concave (821). Consequently, the snapping device (82) and the needle hub with the needle are pulled into the hollow barrel (81) to prevent the medical workers from being pricked and accidentally infected by the used needle when the plunger (84) is backward pulled after syringing.

However, the snapping device (82) is connected to the hollow barrel (81) only by the protrusion (811) being received in the concave (821) in the snapping device (82). Consequently, the snapping device (82) is securely connected to the hollow barrel (81) when the protrusion (811) has a height greater than a depth of the concave (821) to prevent the snapping device (82) from falling into the hollow barrel (81) when mounting the needle hub (83) onto the hollow stub (822) of the snapping device (82). However, the plunger (84) cannot backward pull the snapping device (82) and the needle hub (83) into the hollow barrel (81) after syringing when the connection between the snapping device (82) and the hollow barrel (81) is greater than that between the snapping device (82) and the arrow (842) of the plunger (84) such that the needle will expose out of the hollow barrel (81) and hurt the medical workers. On the contrary, the connector will fall into the hollow barrel (81) when attaching the needle (83) to the snapping device (82).

The present invention has arisen to mitigate and/or obviate the disadvantages of the conventional syringe with a snapping device.

SUMMARY OF THE INVENTION

The main objective of the present invention is to provide an improved syringe with a snapping device for backward pulling the needle into the syringe after syringing to prevent the medical workers from being pricked and accidentally infected by the used needle.

To achieve the objective, the syringe in accordance with the present invention comprises a hollow barrel having an annular shoulder laterally extending from an inner periphery near a front end and two sector apertures defined in and extending through the annular shoulder. The snapping device is detachably secured in the front end of the hollow barrel and includes an annular flange laterally extending therefrom. Two snappers downward extend from the snapping device and engaged to the annular shoulder to longitudinally position the snapping device. A first connector is formed on the snapping device opposite to the hollow stub. A plunger is slidably and partially received in the hollow barrel. A second connector extends from the bulb and is selectively connected the first connector for turning and backward pulling the snapping device into the hollow barrel.

Further benefits and advantages of the present invention will become apparent after a careful reading of the detailed description with appropriate reference to the accompanying drawings.

DETAILED DESCRIPTION OF THE INVENTION

Referring to the drawings and initially to FIGS. 1–5A that show a first embodiment of a syringe with a snapping device for backward pulling the needle into the syringe after syringing in accordance with the present invention. The syringe comprises a hollow barrel (1), a snapping detachably mounted in the hollow barrel (1) and a plunger (15) slidably and partially received in the hollow barrel (1).

The hollow barrel (1) comprises an inner periphery (101), an outer periphery (102), a first end (103) and a second end (104). An annular shoulder (11) inward laterally extends from the inner periphery (101) of the hollow barrel (1) near the first end (103) of the hollow barrel (1).

Figure 1:
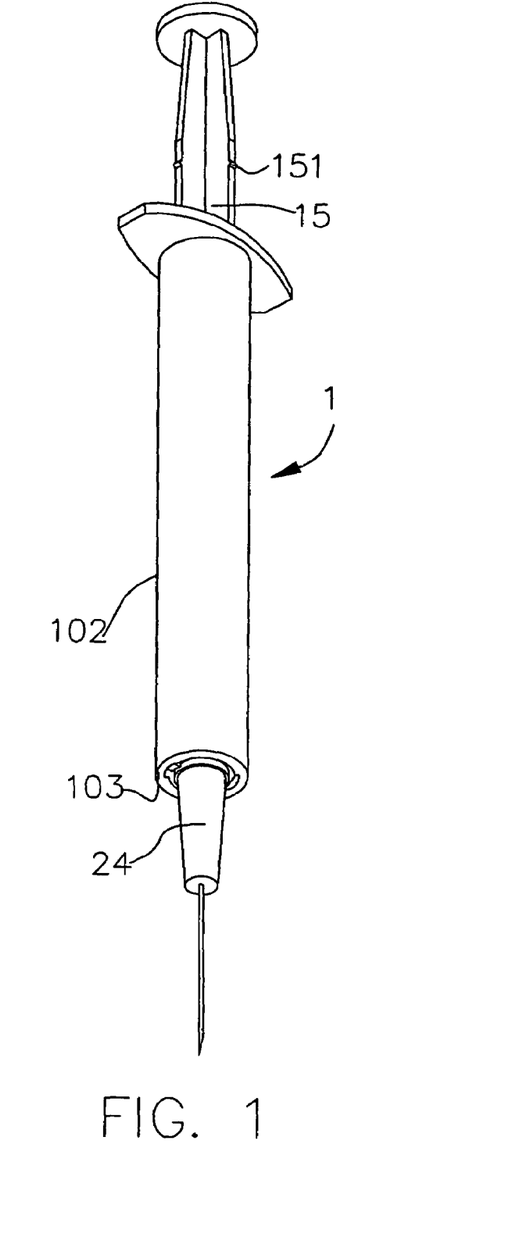
FIG. 1 is a perspective view of a syringe with a snapping device for backward pulling the needle into the syringe after syringing in accordance with the present invention.
Figure 2:
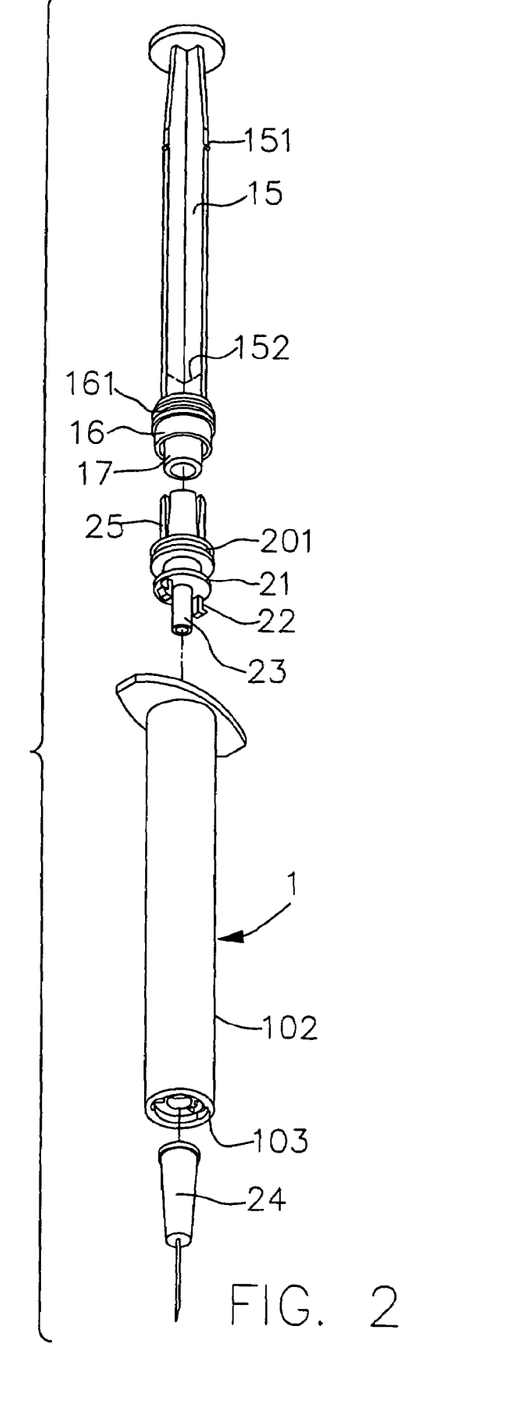
FIG. 2 is an exploded perspective view of the syringe in FIG. 1.
Figure 4:
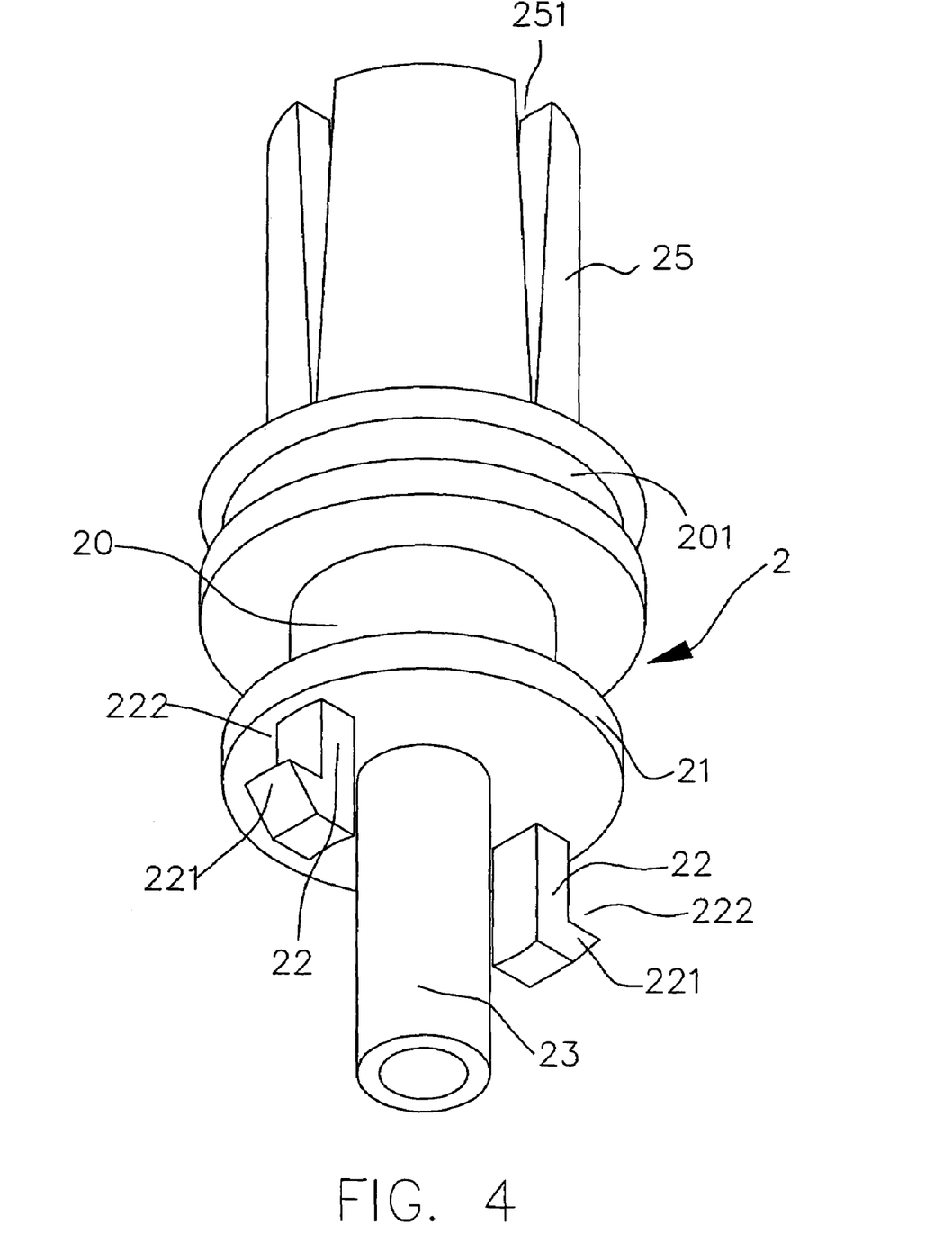
FIG. 4 is a perspective view of the snapping device of the present invention in FIG. 1.
Figure 5A:
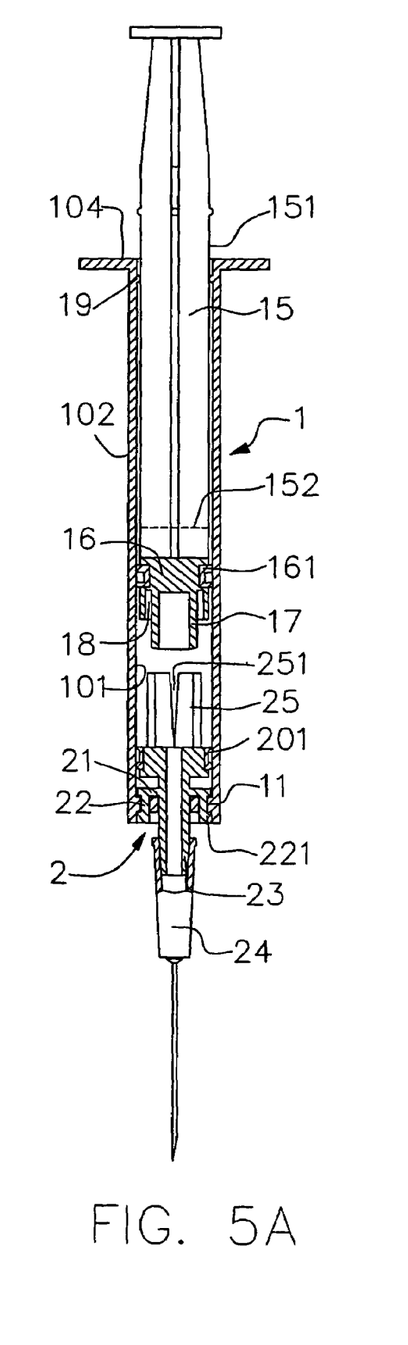
FIG. 5A is a cross-sectional side plan view of the syringe of the present invention in FIG. 1.

The snapping device (2) comprises a body (20) and an O-ring (201) mounted around the body (20). The O-ring (201) securely abuts the inner periphery (101) when the snapping device (2) is mounted in the hollow barrel (1) near the first end (103) of the hollow barrel (1) to prevent the liquid in the hollow barrel (1) from leaking. An annular flange (21) is laterally extending from the body (20) of the snapping device (2) and two snappers (22) downward extend from the annular flange (21). The two snapper (22) diametrically correspond to each other. Each snapper (22) has a hook (221) outwardly extending from a free end of the snapper (22) to define a passage (222) between the hook (221) and the annular flange (21).

Figure 3:
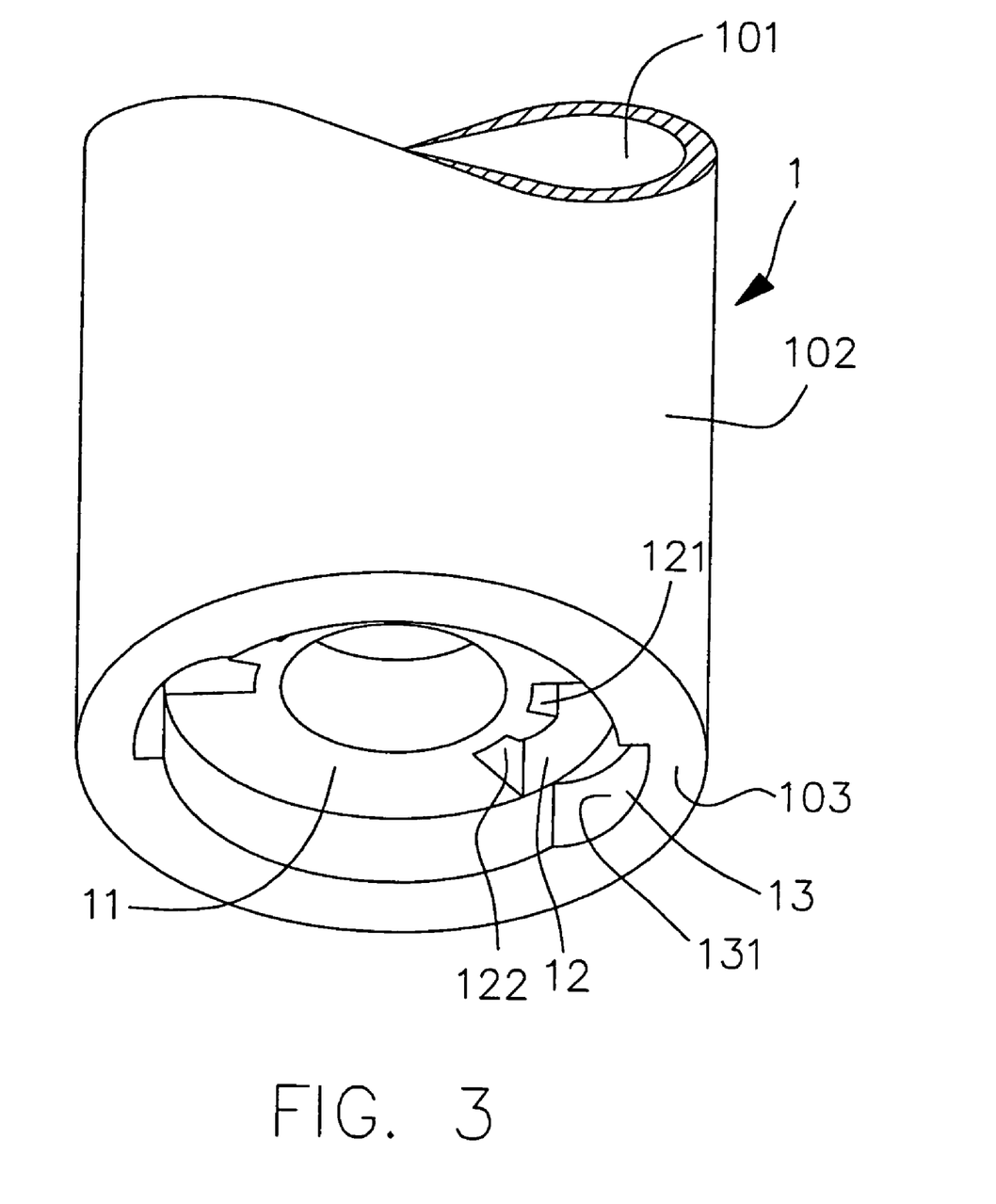
FIG. 3 is a partial perspective view of the hollow barrel of the present invention in FIG. 1.

The hollow barrel (1) includes two arc apertures (12) defined in and extending through the annular shoulder (11). The two apertures (12) allow the two snapper (22) extending through the annular shoulder (11). Each aperture (12) has a first indentation (121) and a second indentation (122) respectively defined in two opposite ends of each of the two apertures (12). The first indentation (121) and the second indentation (122) radially extend toward a center of the hollow barrel (1). The hook (221) is engaged to the annular shoulder (11) and the annular shoulder (11) is partially received in the passage (222) between the hook (221) and the annular flange (21) to longitudinally hold the snapping device in place.

The hollow barrel (1) has two recesses (13) defined in the inner periphery (101) of the first end (103) of the hollow barrel (1) for receiving the hook (221). Each recess (13) has a guiding surface formed on the inner periphery (101) of the hollow barrel (1) and gradually approached relative to the center of the hollow barrel (1). The guiding surface (131) inward pushes the hook (221) to make the hook (221) detach from the annular shoulder (11) and received in the second indentation (122) when the snapping device (2) is rotated relative to the hollow barrel (1).

The snapping device (2) includes a hollow stub (23) centrally extending from the body (20) and through the first end (103) of the hollow barrel (1) when the snapping device (2) is positioned in the first end (103) of the hollow barrel (1). The hollow stub (23) communicates with an interior of the hollow barrel (1). A first connector (25) centrally extends from the body (20) opposite to the hollow stub (23). Multiple slots (251) are longitudinally defined in the first connector (25) such that the first connector (25) can radially expand.

Figure 6:
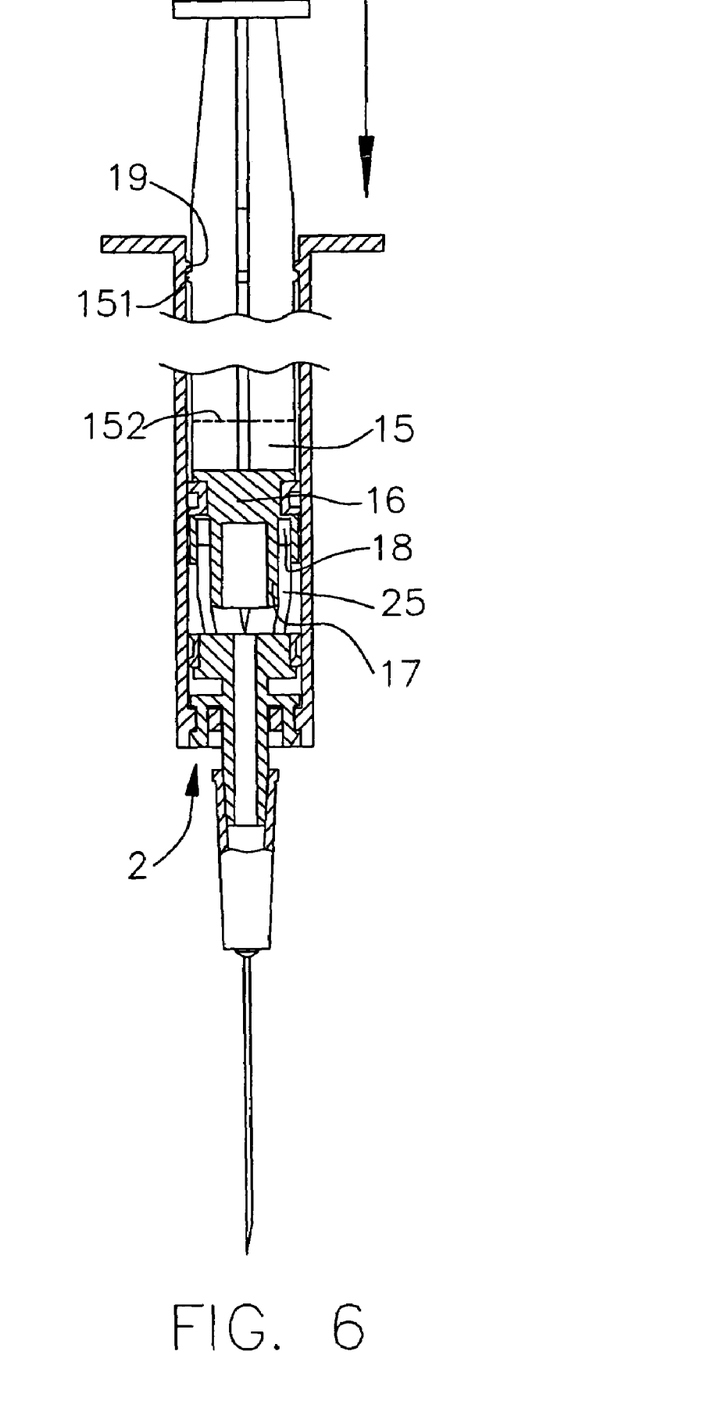
FIG. 6 is a cross-sectional side plan view of the syringe of the present invention when the plunger is connected to the snapping device.

The plunger (15) includes a bulb (16) mounted on one end of the plunger (15) and moved in the hollow barrel (1). An O-ring (161) is mounted around the bulb (16) and securely abuts the inner periphery of the hollow barrel (1) to prevent the liquid in the hollow barrel (1) form leaking. A second connector (17) extends from the bulb (16) toward the first connector (25) and an annular groove (18) is defined surrounding the second connector (17). The second connector (17) has an outer diameter slightly greater than an inner diameter of the first connector (25). Consequently, the first connector (25) slightly expands when the second connector (17) is inserted into the first connector (25). The distal edge of the first connector (25) is securely received in the annular groove (18) in the bulb (16) and binds the second connector (17) after the distal edge of the first connector (25) being received in the annular groove (18) in the bulb (16). Then, the plunger (15) can rotate the snapping device (2) and backward pull the snapping device (2) in the hollow barrel (1).

Figure 10:
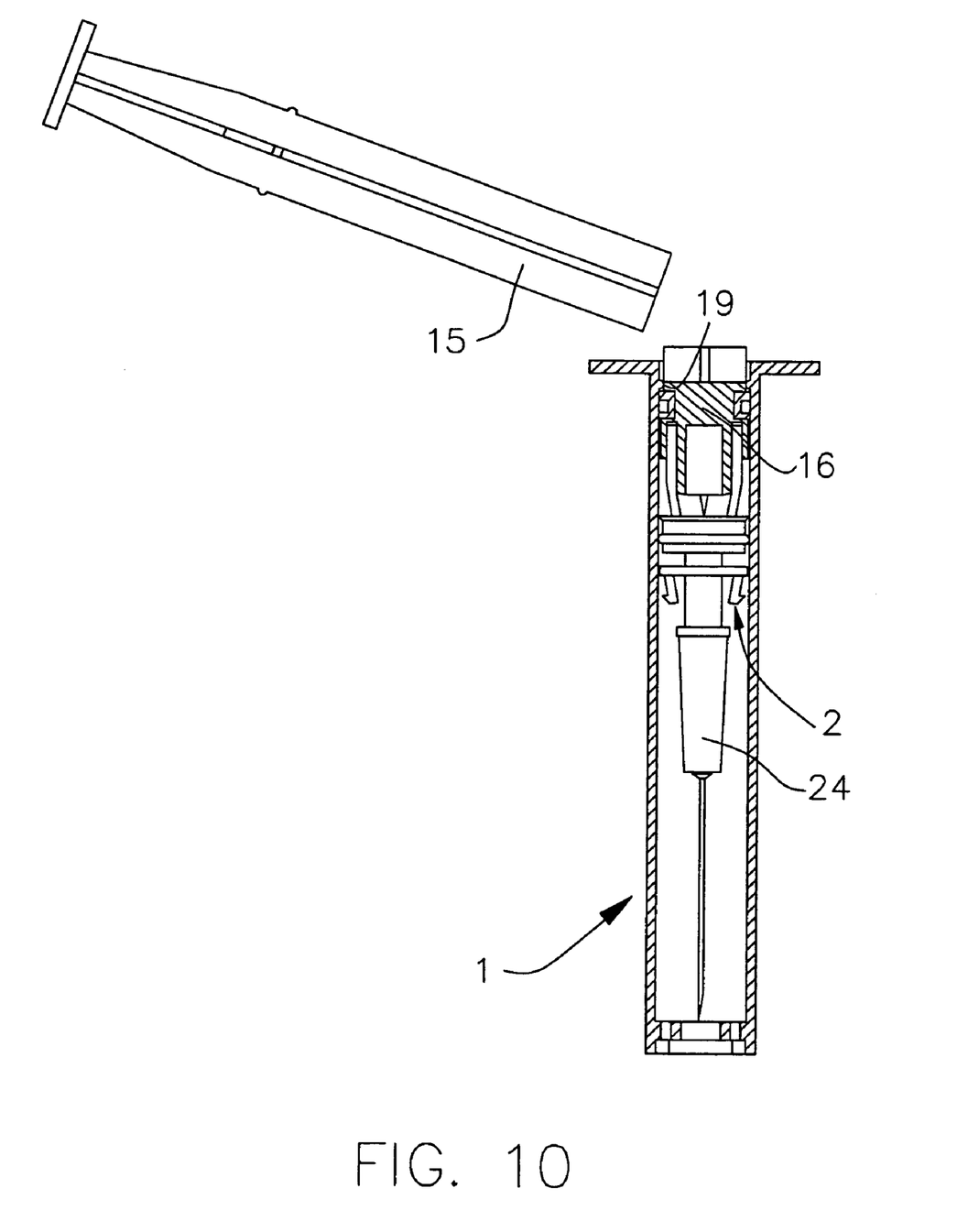
FIG. 10 is an operational plan view of the syringe of the present invention when the needle is backward pulled into the hollow barrel and the plunger is snapped into two pieces.
Figure 11:
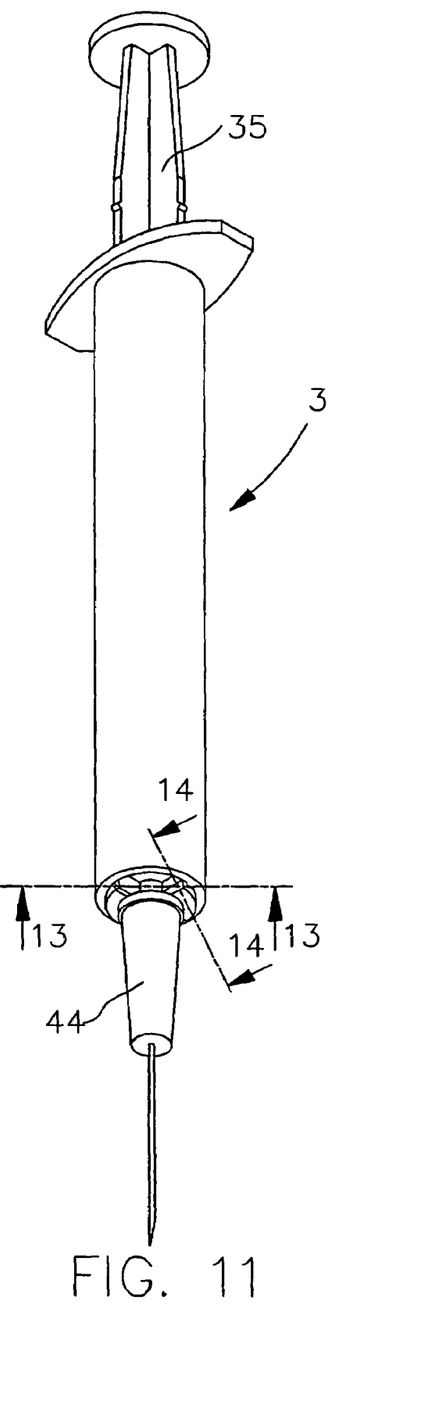
FIG. 11 is a perspective view of a second embodiment of a syringe with a snapping device for backward pulling the needle into the syringe after syringing in accordance with the present invention.
Figure 12A:
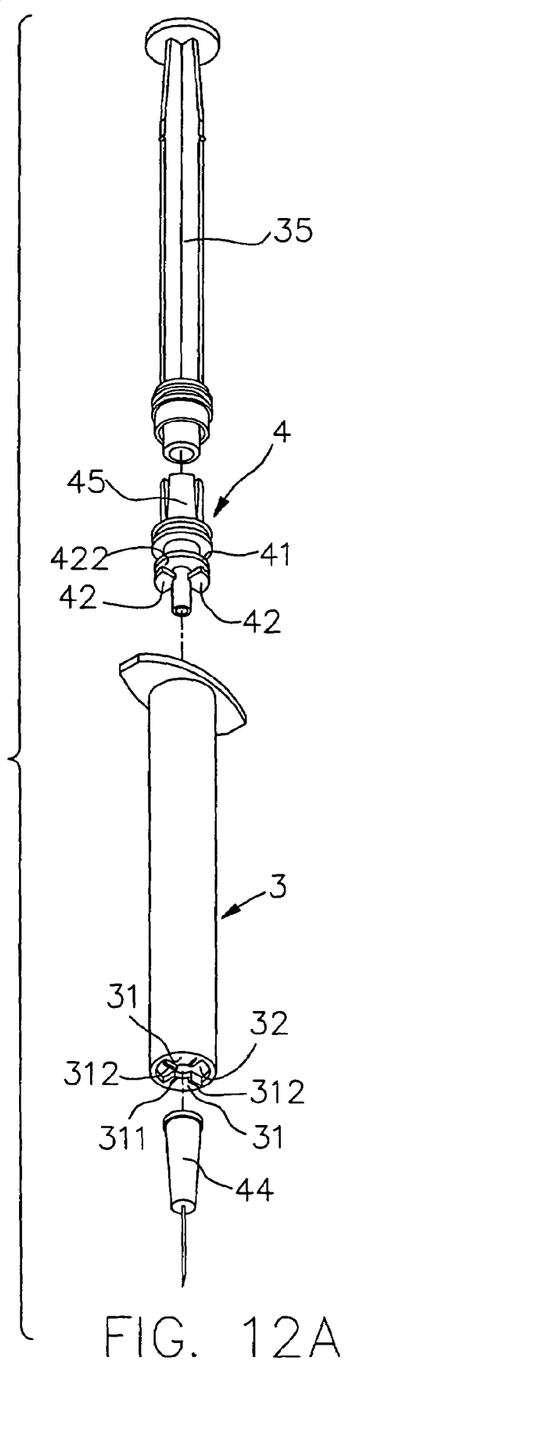
FIG. 12A is an exploded perspective view of the syringe of the present invention in FIG. 11.
Figure 12B:
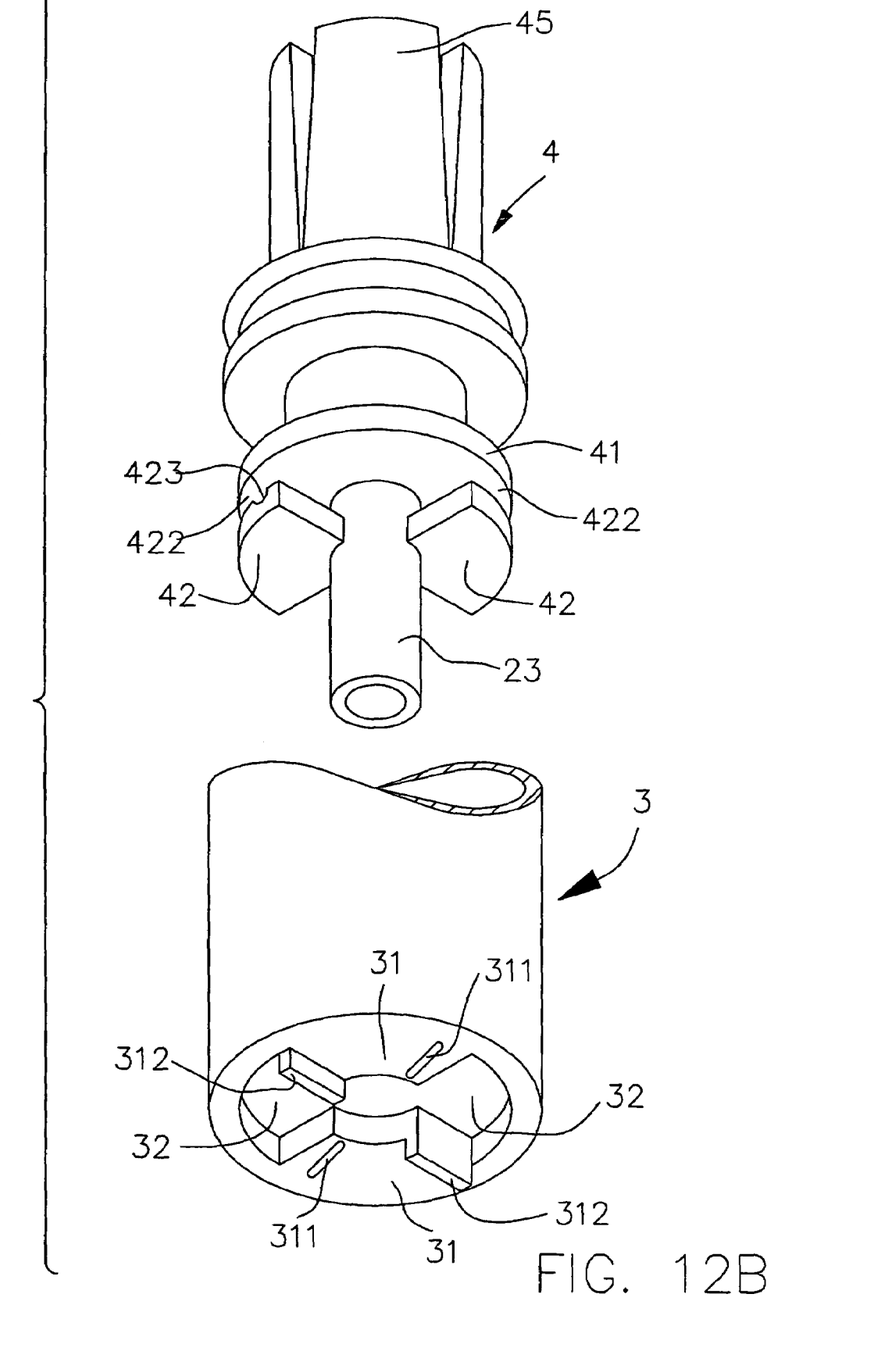
FIG. 12B is a partially exploded perspective view of the syringe of the present invention in FIG. 11.
Figure 13:
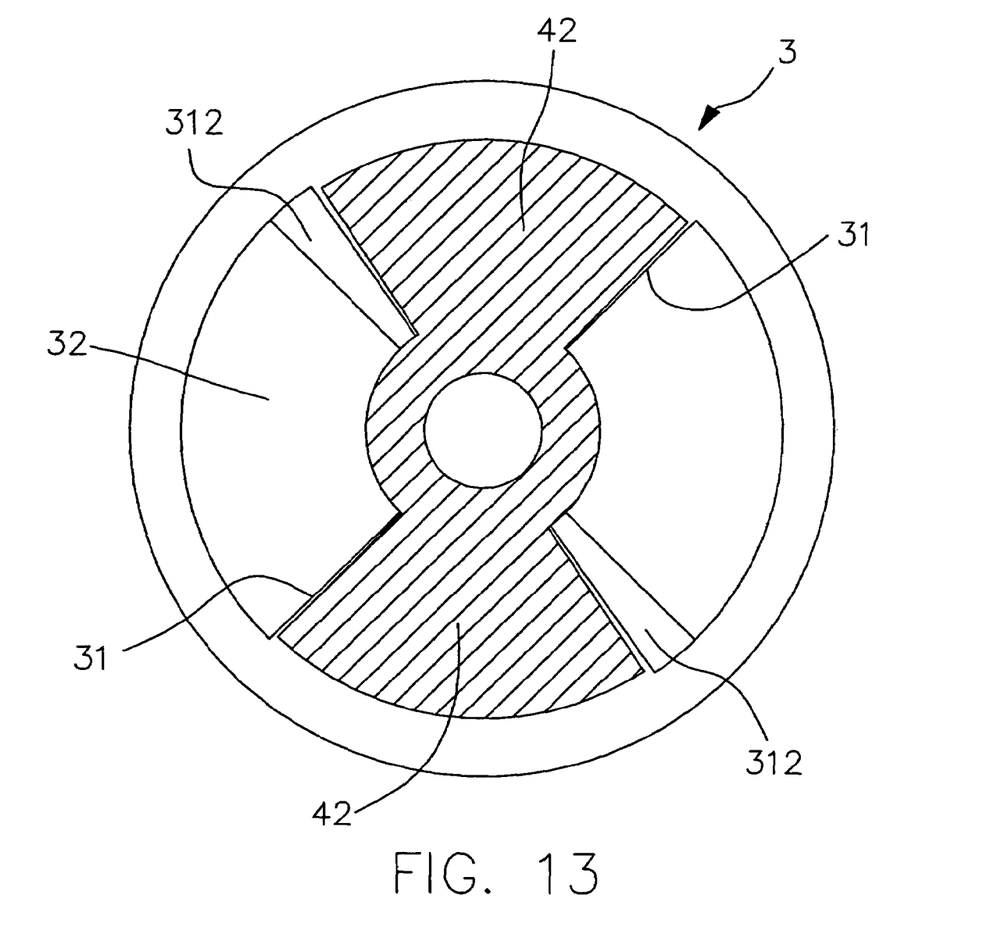
FIG. 13 is a bottom plan view in partial cross-section of the syringe of the present invention in FIG. 11.
Figure 14:
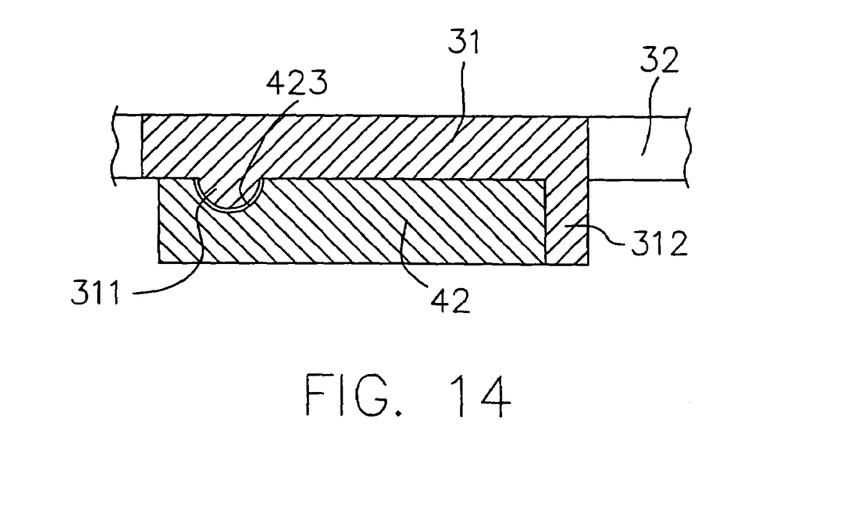
FIG. 14 is partially cross-sectional view of the syringe in FIG. 11 when the needle seat is engaged to the hollow barrel.

The hollow barrel (1) has an annular lip (19) laterally extending from the inner periphery of the hollow barrel (1) near the second end (104) of the hollow barrel (1). The plunger (15) has multiple bosses (151) outward extending from the plunger (15). The annular lip (19) of the hollow barrel (1) and the bosses (151) of the plunger (15) can prevent the second connector (17) from being connected to the first connector (25) before using. A notch (152) is defined in the plunger (15) near the bulb (16) such that the plunger (15) can be easily snapped into two pieces after pulling the snapping into the hollow barrel (1), as shown in FIG. 10.

Figure 5B:
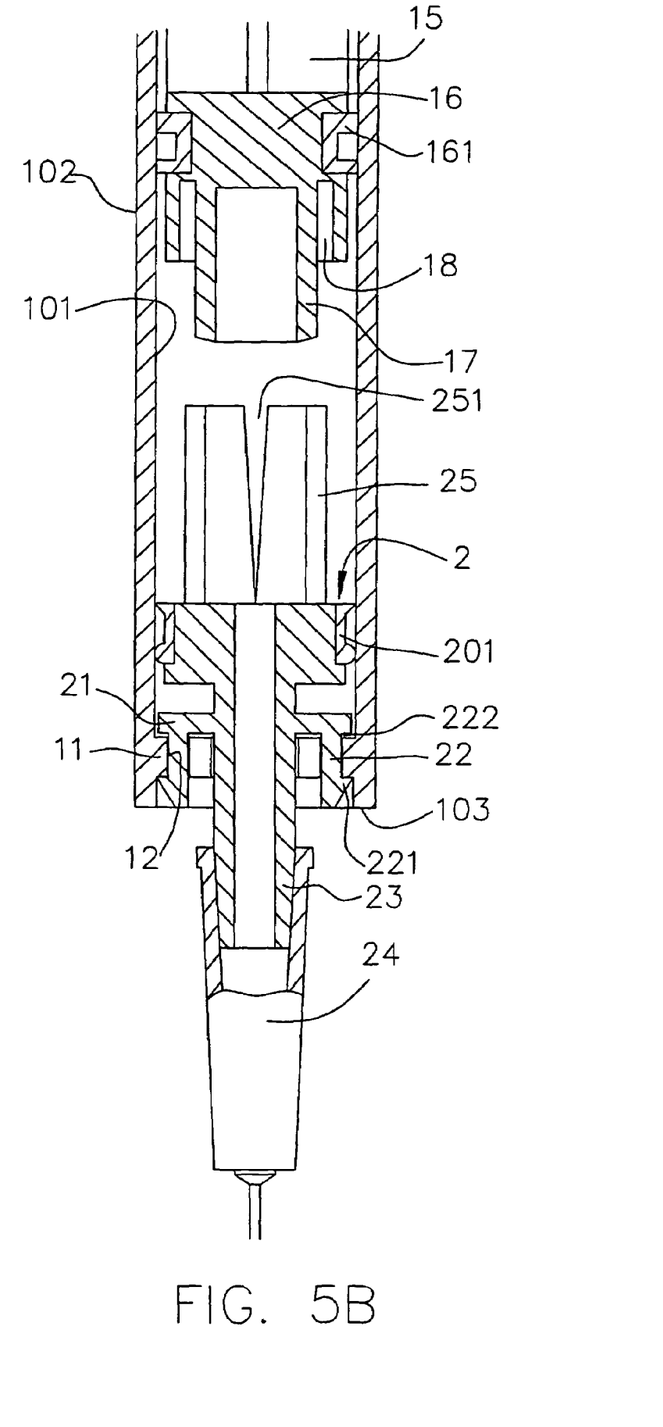
FIG. 5B is partially a cross-sectional side plan view of the syringe of the present invention in FIG. 1.
Figure 7:
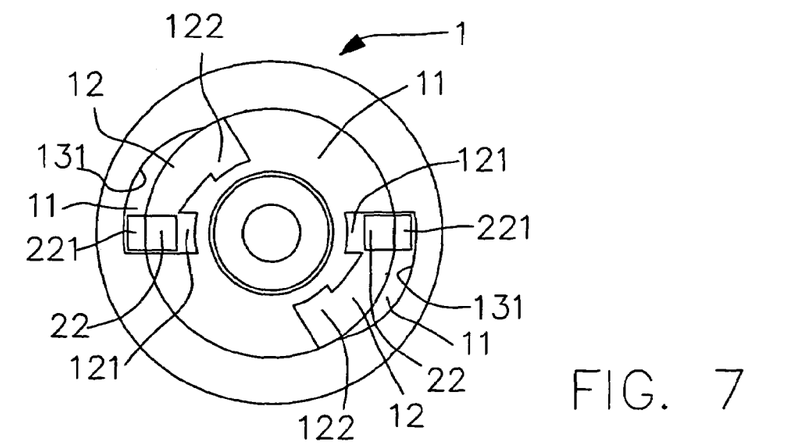
FIG. 7 is a bottom plan view of the syringe of the present invention in FIG. 1 when the needle seat is engaged to the hollow barrel.

With reference to FIGS. 5A, 5B and 7, the hook (221) of the snapper (22) is engaged top the annular shoulder (11) and the annular shoulder (11) is partially received in the passage (222) after the hook (221) moved over the annular shoulder (11) such that the snapping device (2) is longitudinally positioned in the hollow barrel (1) due to the hook (221) and the annular shoulder (11) relative to the hollow barrel (1). Before using the syringe of the present invention, a needle hub (24) with a needle (not numbered) is sleeved on the hollow stub (23) and the snapping device (2) is positioned well. Before chambering medical agent or drawing blood to forward push the plunger (15), the annular lip (19) of the hollow barrel (1) and the bosses (151) of the plunger (15) can prevent the plunger (15) pushed too much to make the second connector (17) connected to the first connector (25).

After syringing, the plunger (15) is moved toward the snapping device (2) and the second connector (17) is connected to the first connector (25) when the bosses (151) moved over the annular lip (19). Then, the plunger (15) can rotate the snapping device (2).

Figure 8:
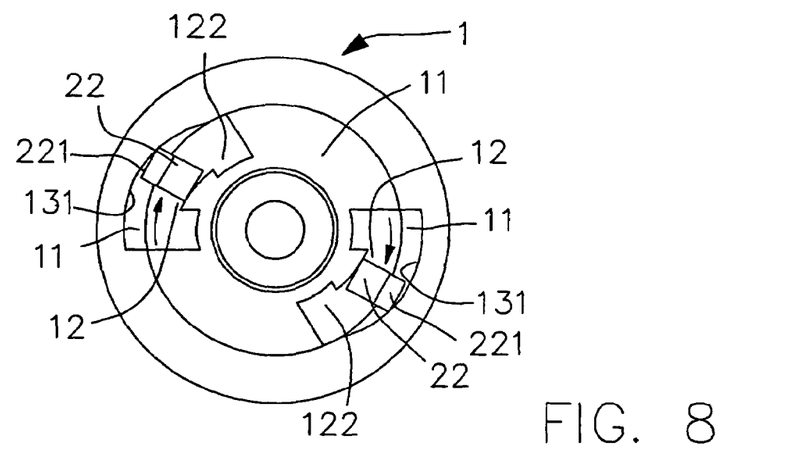
FIG. 8 is operational bottom plan view of the syringe of the present invention in FIG. 1 when the needle seat is rotated.
Figure 9:
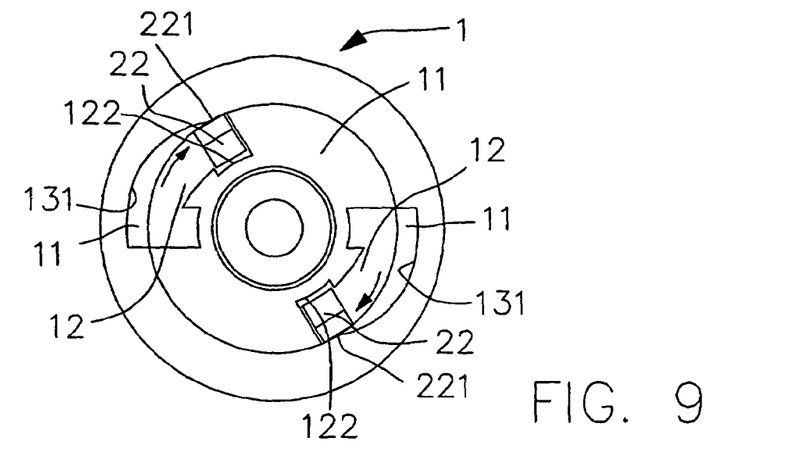
FIG. 9 is a bottom plan view of the syringe of the present invention when the needle seat is disengaged relative to the hollow barrel.

Further with reference to FIG. 8, the guiding surface (131) inward pushes the hook (221) when the snapping device (2) is rotated by the plunger (15). As shown in FIG. 9, the hook (221) is detached from the annular shoulder (11) when being moved from the first indentation (121) to the second indentation (122). Then, the snapping device (2) is in a free condition relative to the hollow barrel (1). Consequently, the plunger (15) can backward pull the snapping device (2) and the needle hub (24) with the needle into the hollow barrel (1) after using to prevent the medical workers from being pricked and accidentally infected by the used needle.

With reference to FIGS. 11 to 14 that show a second embodiment of the connecting type of the snapping device (4) and the hollow barrel (3), the snapping device (4) has two sector wing plates (42) laterally extending from the hollow stub (23) and a passage (422) is defined between the sector wing plate (42) and the annular flange (41). Each sector wing plate (42) has a slit (423) radially defined in each of the two sector wing plates (42). The two slits (423) correspond to each other and face the annular flange (41). The first end of the hollow barrel (3) is an open end and has a two sector flanges (31) laterally inward extending from the inner periphery of the hollow barrel (3). The two sector flanges (31) diametrically correspond to each other and define two sector apertures (32) in the first end of the hollow barrel (3). Each sector flange (31) has a stopper (312) downward extending from one end of each of the two sector flanges (31) and a rib (311) downward extending from each of the two sector flanges (31). Each sector aperture (32) corresponds to a corresponding one of the two sector wing plates (42). To assemble the snapping device (4) and the hollow barrel (3), the snapping device (4) is moved in the hollow barrel (3) and turned when the two sector wing plates (42) pass through the two apertures (32). The sector flange (31) is received in the passage (422) and the rib (311) is received in the slit (423) to hold the snapping device (4) in place and the stopper (312) can prevent the snapping device (4) from rotating too much. The connecting type of the plunger (15) and the snapping device (4) is the same as the first embodiment that is described hereinbefore. The snapping device (4) is turned to make the sector wing plate (42) aligning with the sector aperture (32) when detaching the snapping device (4) form the first end of the hollow barrel (3). Then, the plunger (35) can backward pull the snapping and the needle hub with the needle into the hollow barrel (3).

Figure 15:
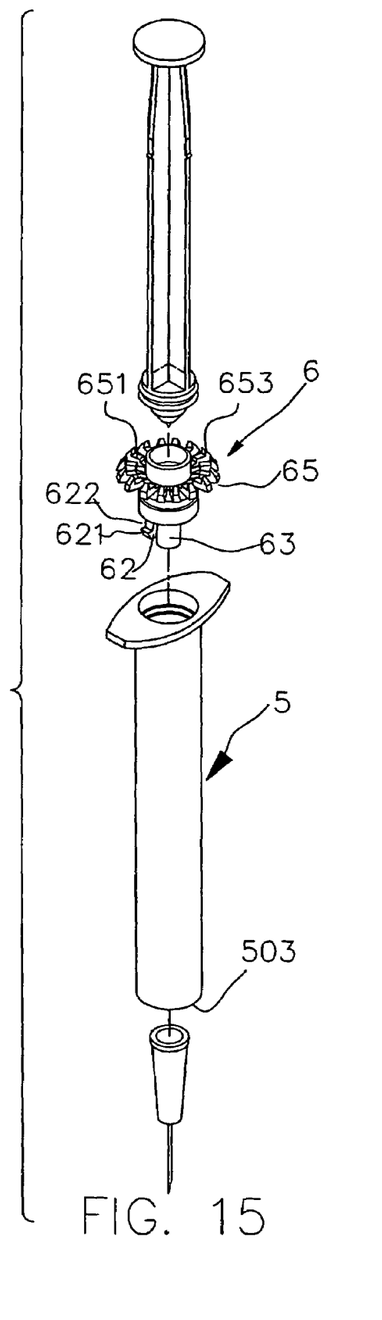
FIG. 15 is an exploded perspective view of a third embodiment of a syringe with a snapping device for backward pulling the needle into the syringe after syringing in accordance with the present invention.
Figure 16:
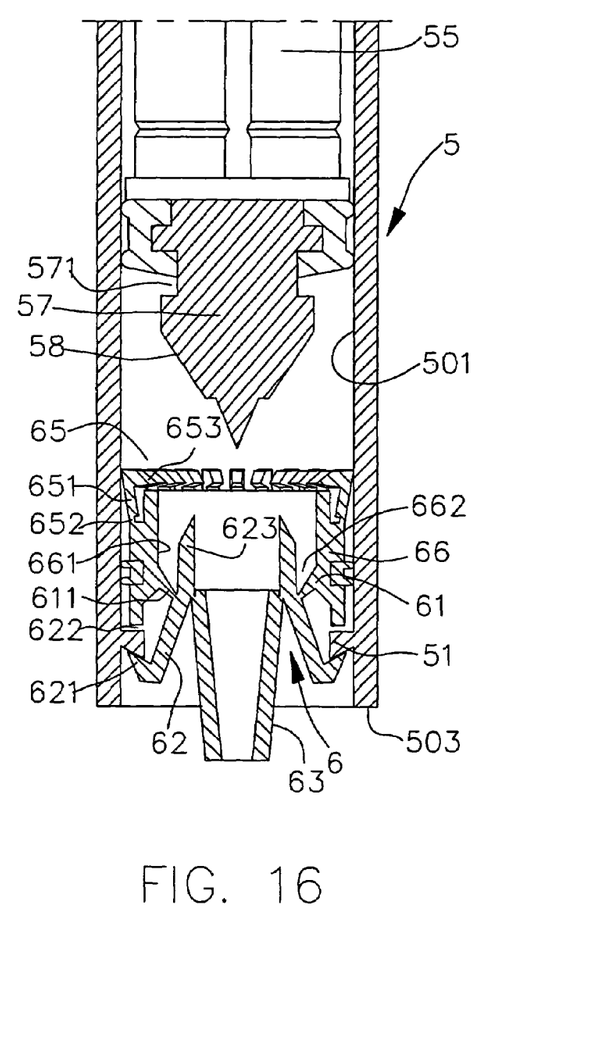
FIG. 16 is a partially cross-sectional view of the syringe of the present invention in FIG. 15 when the plunger is separated from the snapping device.

With reference to FIGS. 15 and 16 that show a third embodiment of connecting type of the snapping device (6) and the hollow barrel (5), the hollow barrel (5) has an annular flange (51) extending from an inner periphery (501) near a front end (503) of the hollow barrel (5). The snapping device (6) includes a hollow stub (63) extending therefrom and through the first end (503) of he hollow barrel (5). A tubular portion (656) is defined in the snapping device (6) and communicating with the hollow stub (63) and the interior of the hollow barrel (5). A first connector (65) is formed on the distal end of the tubular portion (66). A connecting portion (61) is formed between the hollow stub (63) and the tubular portion (66) having an inner wall (661). The snapping device (6) has two snappers (62) extending from the connecting portion (61) and a hook (621) extends from a free end of each of the two snappers (62) to define a passage (622) between the hook (621) and the connecting portion (61). A first resilient portion (611) is formed to connect the connecting portion (61) and the snapper (62). The hook (621) is engaged to the annular flange (51) and the annular flange (51) is partially received in the passage (622) to longitudinally position the snapping device (6) in the hollow barrel (5) when the snapping device (6) is mounted in the hollow barrel (5). The snapping device (6) includes two actuators (623), having recesses (662) and extending therefrom with the tubular portion (66). Each actuator (623) connects to a corresponding one of the two snappers (62).

The first connector (65) includes multiple claws (651) radially outward from the snapping device (6). A second resilient (652) is formed to connect the tubular portion (66). Each claw (651) has a hook (653) inward formed on a free end of each of the claws (651) and defining a circle. The plunger (55) has a second connector (57) secured on one end of the plunger (55) and moved within the hollow barrel (5). A leakproof member (not numbered) is mounted around the second connector (57) and an annular groove (571) is defined in an outer periphery of the second connector (57). The second connector (57) has a diameter slightly greater than that of the circle defined by the hooks (653) to prevent the second connector (57) from being connected to the first connector (65). The second connector (57) has a tapered portion (58) formed on distal end of the second connector (57). The diameter of the tapered portion (58) is gradually reduced relative to the snapping device (6).

Figure 17:
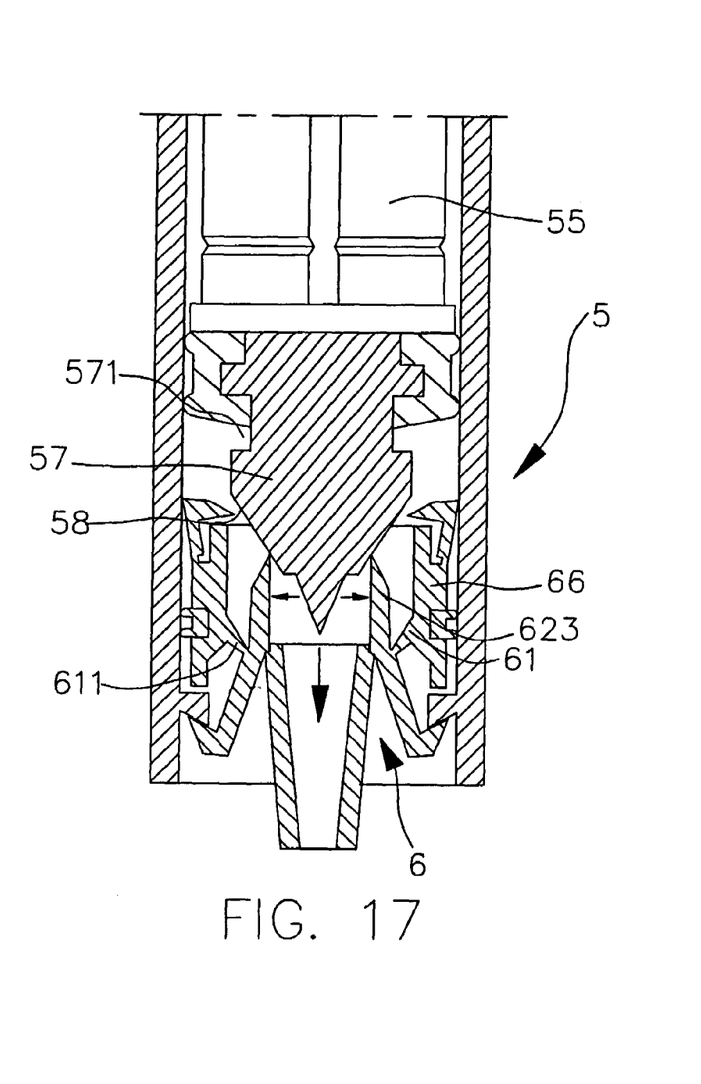
FIG. 17 is a partially cross-sectional view of the syringe of the present invention in FIG. 15 when the plunger is moved toward the snapping device.
Figure 18:
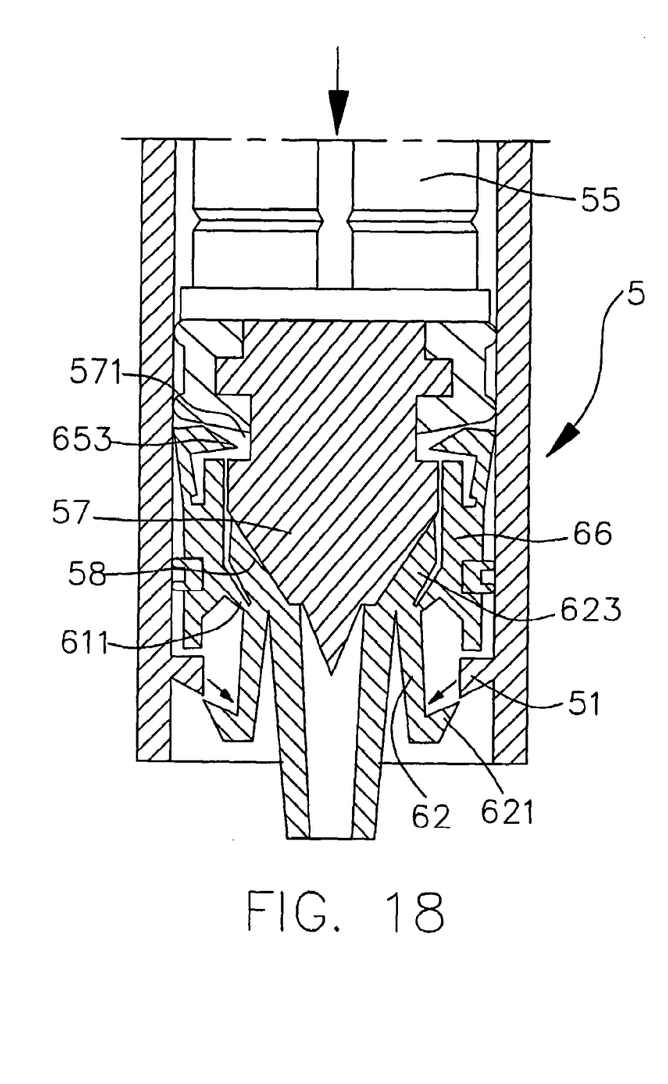
FIG. 18 a partially cross-sectional view of the syringe of the present invention in FIG. 15 when the plunger is connected to the snapping and the snapping device is disengaged relative to the hollow barrel.

With reference to FIGS. 17 and 18, after syringing, the plunger (55) is moved toward the snapping device (6). The hook (653) is engaged to the annular groove (571) in the second connector (57) and the tapered portion (58) outward pushes the actuators (623). Then, the two snappers (62) inward move and the hook (621) of each of the snappers (62) is detached from the annular flange (51). Consequently, the plunger (55) can backward pull the snapping device and the needle hub with the needle into the hollow barrel (5) to achieve the objective of the syringe in accordance with the present invention.

Although the invention has been explained in relation to its preferred embodiment, it is to be understood that many other possible modifications and variations can be made without departing from the spirit and scope of the invention as hereinafter claimed.

What is claimed is:

1. A syringe comprising:
    a hollow barrel having an annular flange extending inward from an inner periphery thereof and located near a first end of the hollow barrel;
    a snapping device detachably secured in the first end of the hollow barrel and having a hollow stub which extends through the first end of the hollow barrel and is adapted to be connected with a needle hub, two snappers connected to the hollow stub and a hook extending from a free end of each of the two snappers, the snapping device having a tubular portion and a connection portion connected between the hollow stub and the tubular portion, a passage defined between the hook and the connecting portion, the annular flange located in the passage and the hooks engaged with the annular flange, the snapping device having two actuators extending therefrom with the tubular portion and respectively connected to the two snappers, a first connector connected to a distal end of the tubular portion and having a plurality of claws extending radially outward therefrom, and
    a plunger movably received in the hollow barrel and having a second connector secured on one end of the plunger, an annular groove defined in an outer periphery of the second connector and a tapered portion formed on distal end of the second connector, a diameter of the tapered portion gradually reduced relative to the snapping device, the actuators being expanded outward when the second connector is inserted between the two actuators and the two snappers move inward to disengage from the annular flange.

2. The syringe as claimed in claim 1, wherein a first resilient portion is formed to connect the connecting portion and the snapper corresponding thereto.

3. The syringe as claimed in claim 1, wherein a second resilient portion is formed to connect the tubular portion to the claws.

4. The syringe as claimed in claim 1, wherein the claws each have a hook inward formed on a free end thereof and define a circle.

5. The syringe as claimed in claim 1, wherein the hollow barrel has an annular lip laterally extending from the inner periphery of the hollow barrel near a second end of the hollow barrel, the plunger has multiple bosses outward extending therefrom such that the annular lip of the hollow barrel and the bosses of the plunger prevent the second connector from being connected to the first connector before using.

6. The syringe as claimed in claim 1, wherein a notch is defined in the plunger near the second connector such that the plunger is snapped into two pieces.

* * * * *